United States Patent [19]

McBride

[11] Patent Number: 4,880,422

[45] Date of Patent: Nov. 14, 1989

[54] REFASTENABLE DIAPER SHEET

[75] Inventor: Robert K. McBride, Jasonville, Ind.

[73] Assignee: Tredegar Industries, Inc., Richmond, Va.

[21] Appl. No.: 215,418

[22] Filed: Jul. 5, 1988

[51] Int. Cl.$^4$ .......................................... A41B 13/02
[52] U.S. Cl. .................................................. 604/389
[58] Field of Search ................ 604/361, 370, 366, 389

[56] References Cited

U.S. PATENT DOCUMENTS

| | | |
|---|---|---|
| 2,714,889 | 8/1955 | Chambers . |
| 3,221,738 | 12/1965 | Ekberg . |
| 3,543,750 | 12/1970 | Meizanis . |
| 3,620,217 | 11/1971 | Gellert . |
| 3,646,937 | 3/1972 | Gellert . |
| 3,683,916 | 8/1972 | Mesek et al. . |
| 3,783,871 | 1/1974 | Sabee . |
| 3,848,594 | 11/1974 | Buell . |
| 3,874,386 | 4/1975 | Kozak . |
| 3,881,489 | 5/1975 | Hartwell . |
| 3,951,149 | 4/1976 | Ness et al. . |
| 3,987,793 | 10/1976 | Milnamow . |
| 3,999,546 | 12/1976 | Feldman et al. . |
| 4,014,339 | 3/1977 | Tritsch . |
| 4,014,340 | 3/1977 | Cheslow . |
| 4,020,842 | 5/1977 | Richman et al. . |
| 4,041,949 | 8/1977 | Kozak . |
| 4,049,001 | 9/1977 | Tritsch . |
| 4,055,181 | 10/1977 | Tritsch . |
| 4,074,004 | 2/1978 | Bateson et al. . |
| 4,100,922 | 7/1978 | Hernandez . |
| 4,158,363 | 6/1979 | Schaar . |
| 4,183,457 | 1/1980 | Loughley et al. . |
| 4,194,507 | 3/1980 | Ness et al. . |
| 4,207,895 | 6/1980 | Schaar . |
| 4,209,016 | 6/1980 | Schaar . |
| 4,214,028 | 7/1980 | Shortway et al. . |
| 4,227,530 | 10/1980 | Schatz . |
| 4,237,889 | 12/1980 | Gobran . |
| 4,253,461 | 3/1981 | Strickland et al. . |
| 4,276,982 | 7/1981 | Sibrava . |
| 4,296,750 | 10/1981 | Woon et al. . |
| 4,330,888 | 3/1982 | Klepfer . |
| 4,345,597 | 8/1982 | Tritsch . |
| 4,369,786 | 1/1983 | Miller . |
| 4,436,520 | 3/1984 | Lipko et al. . |
| 4,540,415 | 9/1985 | Korpman . |
| 4,573,986 | 3/1986 | Minetola . |
| 4,578,071 | 3/1986 | Buell . |
| 4,582,550 | 4/1986 | Sigl . |
| 4,622,036 | 11/1986 | Goodrum . |
| 4,626,252 | 12/1986 | Nishizawa et al. . |

FOREIGN PATENT DOCUMENTS

| | | |
|---|---|---|
| 148587 | 7/1985 | European Pat. Off. . |
| 3419623 | 11/1985 | Fed. Rep. of Germany . |
| 1320628 | 6/1973 | United Kingdom . |
| 1342115 | 12/1973 | United Kingdom . |

*Primary Examiner*—C. Fred Rosenbaum
*Attorney, Agent, or Firm*—Emch, Schaffer, Schaub & Porcello Co.

[57] ABSTRACT

A refastenable disposable diaper having a backsheet of low density polyethylene and polypropylene.

20 Claims, No Drawings

REFASTENABLE DIAPER SHEET

This application is a continuation of application Ser. No. 898,404, filed Aug. 20, 1986, now abandoned.

BACKGROUND OF THE INVENTION

This invention relates to disposable diapers having normally tacky and pressure-sensitive adhesive tape closures and is particularly concerned with composite closures (i.e., closures made with more than one tape) that can be opened and refastened without destroying either the diaper or the tape.

The invention especially relates to a thermoplastic monolayer film suitable for use as a refastenable diaper backsheet comprising a blend of polyolefins particularly polypropylene and polyethylene.

At least as early as 1955 it had been suggested to use strips of normally tacky and pressure-sensitive adhesive tape to hold conventional cloth diapers on an infant; see, e.g., Chambers U.S. Pat. No. 2,714,889 and Ekberg U.S. Pat. No. 3,221,738. A few years later, when disposable diapers became extremely popular, strips of pressure-sensitive adhesive tape were again employed as closures; see, e.g., Gellert U.S. Pat. No. 3,620,217.

A disposable diaper typically has a thin, flexible, stretchy low density polyethylene film cover, an absorbent filler on the inside of the cover, and a porous inner liner overlying the filler. Such a diaper is positioned at the crotch of an infant, the two ends of the diaper extending, respectively, toward the front and back. Adjacent edges of the diaper at each side are then either positioned next to each other or overlapped, a strip of pressure-sensitive adhesive tape being adhered to the cover at the border adjacent each of the two edges and holding the diaper closed. Because most pressure-sensitive adhesives bond firmly to the thin polyethylene diaper cover, it is almost impossible to open the tape closure without destroying the tape and/or the diaper cover in the process.

After a tape closure has been opened, it is frequently discovered that the diaper has not been soiled and hence that there is no need to replace it. If the cover has not been torn, a second strip of tape can sometimes be applied as a replacement closure, but this is often inconvenient. As a result, considerable work has been undertaken to develop a tape diaper closure that is not only capable of bonding firmly to the diaper cover, but is also capable of non-destructive removal and replacement. Closures of this type have generally involved a combination of two or more tapes, one of which remains permanently adhered to one edge of the diaper and is removably adhered to a so-called "target tape" mounted on the other edge of the diaper. Examples of such products are shown in Ness et al, U.S. Pat. No. 3,951,149, Milnamow U.S. Pat. No. 3,987,793, Feldman et al U.S. Pat. No. 3,999,546, and Richman et al U.S. Pat. No. 4,020,842.

The patents referred to in the preceding paragraph do not discuss the manner in which the closures are prepared. Typically in making such closures, the manufacturers of diapers mount rolls of the appropriate tape in their equipment, combining them to form a composite strip of tape, the width of which is substantially the same as the length of the diaper closure to be fabricated. The composite roll is then severed at right angles to the edges of the composite strip at intervals corresponding to the width of the desired tape closure and adhered at an appropriate location along the border adjacent the sides of the diaper. Although this manufacturing process is effective, many relatively small manufacturers are unable to provide the machinery necessary to accomplish the superimposition of several rolls of tape. As a result, it is important for a tape supplier to provide the manufacturers with a composite roll, made up of two or more specific tapes from which closures may readily be prepared.

A variety of diapers have been made with resealable tapes or refastenable disposable diapers. Representative are U.S. Patents 4,049,001, 4,055,181, 4,158,363, 4,227,530, 4,296,750, 4,345,597, and 4,369,786; European Patent Application 148,587; and West German Patent No. 3,419,623.

U.S. 4,330,888 discloses a disposable bib or napkin with an upper edge portion carrying a pressure-sensitive adhesive capable of releasably adhering to the clothing or body of a user. British patents 1,320,628 and 1,342,115 disclose adhesive sheets or adhesive composite material which will releasably adhere to itself.

Additional diapers with tape fastening systems are described in U.S. 3,646,937, U.S. 3,848,594, U.S. 3,874,386, U.S. 3,951,149, U.S. 3,987,793, U.S. 3,999,546, U.S. 4,014,339, U.S. 4,014,340, U.S. 4,020,842, U.S. 4,041,949, U.S. 4,074,004, U.S. 4,194,507, U.S. 4,207,895, U.S. 4,209,016, U.S. 4,237,889, U.S. 4,573,986, and U.S. 4,578,071.

A wide variety of refastenable diapers have been constructed with varying degrees of success. One type of product has a one-piece pressure sensitive tape tab system which permits multiple fastening and refastening of the pressure-sensitive diaper tape tab to the embossed thermoplastic film used as the outside or backsheet of the diaper.

An object of this invention is to provide a resin composition for making an embossed thermoplastic film backsheet which with a suitable fastening tape can be fastened and refastened as many times as desired.

It is an important object of the present invention to provide a thermoplastic resin composition for making an embossed monolayer thermoplastic film which may be effectively utilized as the outside or backsheet of refastenable disposable diapers having a refastenable diaper backsheet film having improved tensile strength.

Another object of the invention is to provide a thermoplastic resin composition suitable for making a refastenable backsheet which may be either blown film constructed or cast-film constructed.

Other objects and advantages of the invention will be more readily apparent from a reading of the description hereinafter.

SUMMARY OF THE INVENTION

The present invention provides a refastenable disposable diaper having a backsheet of thermoplastic film comprised of a blend of polypropylene and low density polyethylene. Linear low density polyethylene or linear medium density polyethylene may be used in whole or in part as the low density polyethylene.

DESCRIPTION OF THE PREFERRED EMBODIMENTS

An embossed monolayer thermoplastic film suitable for use as an outside sheet or backsheet of a refastenable disposable diaper preferably has a transverse direction (T.D.) tensile strength (stress) value at low elongations (<25%) between one pound and three pounds; T.D.

tensile strength @ break values above two pounds; gloss @ 45 values (non-treated side) ≦8; slip C.O.F. (coefficient of friction) values (non-treated side) between 0.3 and 0.9 and tape peel force value between one pound and two pounds at nominal film thicknesses (≦1.5 mils).

A refastenable diaper sheet can be made using either blown-film or cast-film extrusion. Blown-film extrusion is preferred because films so made will be more balanced in the machine and transverse directions and have higher toughness values.

Non-refastenable embossed monolayer thermoplastic films used as the outside sheet or backsheet of a disposable diaper have been made largely of low density polyethylene (LDPE) resin blended with white pigments and slip additives as required to obtain the opacity (ash) and slip, coefficient of friction (C.O.F.) values needed. With a film thickness of about 1.5 mils, such resin provides a suitable refastenable diaper backsheet. At film thicknesses of less than about 1.5 mils, films of such resins don't have sufficient transverse direction (T.D.) tensile strength (stress) values at low elongations (≦25%) and consequently the film tends to tear or excessively distort as a pressure-sensitive diaper tab is peeled off. To boost the low T.D. tensile strength (stress) values, polyolefins such as high density polyethylene (HDPE) or medium density linear polyethylene (LMDPE) are added to the resin blend for making the film. Larger amounts of each (percent by weight) are required to obtain the desired stress value as nominal film thickness decreases.

Although these polyolefin blends may produce thermoplastic films of the desired T.D. tensile strength (stress) at low elongations, the film may have lowered tape adhesion, lowered drop dart impact (increased splittiness) and less than desired slip C.O.F.

At nominal film thicknesses of 1.0-1.5 mils, conventional LDPE film extrusion equipment is detrimentally influenced by the high head pressure and torque requirements of the high loadings (percent by weight) of HDPE or MDLPE required to obtain the T.D. tensile strength (stress) values needed for refastenability.

It has been discovered that blending from about three weight percent to about 30 weight percent polypropylene with LDPE, LLDPE, LMDPE, or mixtures of any two of the three resins, monolayer films can be produced which have the desired refastenability characteristic, i.e. increased T.D. tensile strength (stress) at elongations and increased tape adhesion without significant degradation of other film physical properties.

About 5-25 weight percent polypropylene is preferred, with about 10-20 weight percent polypropylene being most preferred.

For monolayer films, the gauge of the film should be about 1.0 to 1.5 mils.

Some examples of monolayer thermoplastic films suitable for refastenable backsheets of disposable diapers are set forth in Table I.

TABLE I

MONOLAYER FILMS

RESIN BLEND (Percent by Weight)

| P.P. | LDPE | LLDPE | LMDPE | White Concentrate | Gauge (Mils) |
|---|---|---|---|---|---|
| 7 | 86 | | | 7 | 1.2 |
| 5 | 88.5 | | | 6.5 | 1.2 |
| 10 | 83 | | | 7 | 1.1 |
| 10 | 83 | | | 7 | 1.2 |
| 11 | 83 | | | 6 | 1.3 |

TABLE I-continued

MONOLAYER FILMS

RESIN BLEND (Percent by Weight)

| P.P. | LDPE | LLDPE | LMDPE | White Concentrate | Gauge (Mils) |
|---|---|---|---|---|---|
| 12 | 83 | | | 5 | 1.4 |
| 20 | 50 | 23 | | 7 | 1.1 |
| 10 | 60 | | 25 | 5 | 1.4 |
| 15 | 55 | | 25 | 5 | 1.4 |
| 20 | 55 | | 20 | 5 | 1.4 |
| 10 | 65 | | 20 | 5 | 1.4 |
| 10 | 45 | | 40 | 5 | 1.4 |
| 15 | 50 | | 30 | 5 | 1.4 |

For the purpose of this table the following are identified:
P.P. = Polypropylene; 2 melt flow; .900 density; homopolymer
LDPE = Low density polyethylene; 1.3 melt index; .925 density; liner grade
LLDPE = Linear low density polyethylene; 1.0 melt index; .917 density
LMDPE = Linear medium density polyethylene; 1.0 melt index; .935 density Coextruded or multilayer films are also suitable for use as a refastenable diaper backsheet. Such films should have a core layer of about 50-100 percent polypropylene. The values for the monolayer films are applicable to the coating layers of coextruded films.

The core of a 1.0 mil coextruded film having 0.2 mil outer coatings as illustrated in Table II.

TABLE II

COEXTRUDED OR MULTILAYER FILM
RESIN BLEND (Percent by Weight)

| | Core 0.6 Mil |
|---|---|
| P.P. | 60 |
| LLDPE | 33 |
| White Concentrate | 7 |

In embossed monolayer films containing polypropylene in combination with linear low density polyethylene and/or linear medium density polyethylene, the advantages of each of the resins is obtained. High stress and high tape adhesion qualities of polypropylene are obtained and the high impact values and high tensile strength values of the linear polyethylenes are obtained, thereby providing a film with significantly better overall physical properties than those customarily used in diaper backsheets. Stress at low elongations (≦25 percent) and tape adhesion are also similarly improved in coextruded films containing polypropylene.

In Table III, a comparison is shown between LDPE film and films of various blends. It is readily seen that films containing polypropylene have increased adhesion values and increased T.D. stress @ 10%.

TABLE III

T.D. STRESS AND 120° TAPE ADHESION VALUE
FOR MIXED RESIN BLENDS

| Blend (Percent by Weight) | | | | | T.D. Stress @ 10% (Grams) | 120° Tape Adhesion Value Grams |
|---|---|---|---|---|---|---|
| LDPE | LMDPE | HDPE | P.P. | Wh. Con. | | |
| 93 | | | | 7 | 400 | 295 |
| 83 | 10 | | | 7 | 464 | 286 |
| 88 | 5 | | | 7 | 470 | 329 |
| 83 | | 10 | | 7 | 525 | 351 |
| 73 | | 20 | | 7 | 650 | 348 |
| 88 | | | 5 | 7 | 515 | 380 |
| 83 | | | 10 | 7 | 560 | >425 |

For the purposes of this table, the following are identified:

TABLE III-continued

T.D. STRESS AND 120° TAPE ADHESION VALUE
FOR MIXED RESIN BLENDS

| Blend (Percent by Weight) | | | | | T.D. Stress @ 10% (Grams) | 120° Tape Adhesion Value Grams |
|---|---|---|---|---|---|---|
| LDPE | LMDPE | HDPE | P.P. | Wh. Con. | | |
| 73 | | | 20 | 7 | 804 | >425 |

LDPE — Low Density Polyethylene
LMDPE — Medium Density Linear Polyethylene
HDPE — High Density Polyethylene
P.P. — Polypropylene
Wh. Con. — White Concentrate In Table IV, comparisons between similar films with and without polypropylene are illustrated. It is readily seen that films containing polypropylene have increased T.D. tensile strength (stress) at low elongations ($\leq 25$ percent) and increased tape adhesion.

TABLE IV

T.D. TENSILE STRENGTH (STRESS) AND TAPE
ADHESION OF COMPARABLE FILMS WITH AND
WITHOUT POLYPROPYLENE

| Blend (Weight Percent) | | | Embossing Pattern | Gauge (Mils) | T.D. Stress (Grams) | Tape Adhesion (Grams) |
|---|---|---|---|---|---|---|
| LDPE | P.P. | Wh. Con. | | | | |
| 93 | | 7 | FSII-B | 1.2 | 651 | 417 |
| 86 | 7 | 7 | FSII-B | 1.2 | 735 | 545 |
| 93 | | 7 | M-C | 1.2 | 494 | 299 |
| 84 | 8 | 8* | M-C | 1.2 | 617 | 425 |
| 93 | | 7 | FSII-B | 1.0 | 586 | 294 |
| 83.5 | 9.5 | 7 | FSII-B | 1.0 | 640 | 403 |
| 93 | | 7 | FSI-B | 1.35 | 660 | 467 |
| 86.5 | 7 | 6.5 | FSI-B | 1.35 | 800 | 571 |
| 93 | | 7 | M-C | 1.2 | 606 | 296 |
| 86 | 7 | 7 | M-C | 1.2 | 703 | 366 |

For the purposes of this table, the following are identified:
*Beige
FSII — Fine Square II
FSI — Fine Square I
B — Blown
M — Matte
C — Cast
LDPE — Low Density Polyethylene
P.P. — Polypropylene
Wh. Con. — White Concentrate A disposable diaper comprises in general, a facing sheet defining a diaper inside surface for direction toward an infant, a moisture-impervious backsheet substantially coextensive with the facing sheet and defining a diaper outside surface, an absorbent panel positioned between the facing sheet and the backsheet, and an adhesive tab fastener means. On a refastenable or releasable tape closure, the tape or tab has a free end and a fixed end attached to the diaper. The free end of the tab has an adhesive which is adapted to be releasably affixed to the backsheet.

Refastenable diapers come in a variety of detailed constructions and releasable tapes. An example of such a diaper is illustrated in U.S. 4,330,888, and which patent is specifically incorporated herein.

The present invention provides a unique backsheet for such a refastenable disposable diaper.

A preferred diaper backsheet is constructed of a resin blend comprising by weight percent, about 7 percent polypropylene, about 86 percent low density polyethylene and about 7 percent white concentrate.

A most preferred backsheet is constructed of a resin blend comprising by weight percent, about 12 percent polypropylene, about 83 percent low density polyethylene and about 5 percent white concentrate.

It can readily be appreciated that the instant invention can be incorporated in a variety of diaper constructions and releasable tape constructions. It is essential though that the diaper backsheet comprise or be made of sufficient polypropylene as to provide the desired strength and refastenability feature.

The foregoing disclosure and description of the invention is illustrative and explanatory thereof and various changes in the illustrated film or diaper construction may be made within the scope of the appended claims without departing from the spirit of the invention.

What is claimed is:

1. A refastenable disposable diaper comprising a facing sheet, a backsheet, an absorbent panel positioned between said facing sheet and said backsheet and an adhesive tab fastener means having a first end fixedly attached to said backsheet and a second end refastenably attachable to said backsheet, said backsheet being characterized by comprising a resin blend consisting essentially of polypropylene and a polyethylene selected from the group consisting of LDPE, LLDPE, LMPDE or a mixture of any two of the foregoing in which from 3 to 30 weight percent of the resin blend is polypropylene, and by (ii) having a transverse direction tensile strength value at 10 percent elongation of at least 515 grams and a 120° tab adhesion value of at least 380 grams, whereby said second end of said tab fastener is non-destructably detachable from said backsheet.

2. The diaper of claim 1 wherein the polypropylene comprises about 5 to 25 weight percent of the resin blend.

3. The diaper of claim 1 wherein the polypropylene comprises about 10 to about 20 weight percent of the resin blend.

4. The diaper of claim 1 wherein the backsheet is a monolayer film having a gauge of about 1.0 to about 1.5 mils.

5. The diaper of claim 1 wherein the backsheet is constructed of a resin blend comprising by weight percent, about 7 percent polypropylene, about 86 percent low density polyethylene and about 7 percent white concentrate.

6. The diaper of claim 1 wherein the backsheet is constructed of a resin blend comprising by weight percent, about 12 percent polypropylene, about 83 percent of said polyethylene and about 5 percent white concentrate.

7. The diaper of claim 1 wherein the backsheet is a coextruded multilayer film comprising (a) a polypropylene inner core of about 50 to about 100 percent polypropylene, and (b) coating layers each composed of a resin blend of polypropylene and said polyethylene in which from about 3 to about 30 weight percent of the resin blend is polypropylene.

8. The diaper of claim 7 wherein the backsheet is a multilayer film of a minimum gauge of about 0.9 mils.

9. The diaper of claim 1 wherein the backsheet is an embossed monolayer blown film having a nominal thickness of about 1.0 to about 1.5 mils made from a resin blend of said polyethylene and polypropylene, the polypropylene constituting 5 to 25 weight percent of the blend.

10. The diaper of claim 9 wherein said film additionally contains an opacifying amount of opacifying pigment.

11. The diaper of claim 2 wherein the backsheet is of a resin blend which consists essentially of 10 to 20 weight percent polypropylene, from about 20 to about 40 weight percent LMDPE, from about 45 to about 64 weight percent LDPE and wherein said resin blend in addition contains up to 7 weight percent of white concentrate.

12. A backsheet for refastenable disposable diapers consisting essentially of a blend of a polyethylene resin selected from the group consisting of LDPE, LLDPE, LMDPE or a mixture of any two of the foregoing, a polypropylene resin, and a color pigment, about 3 to about 30 weight percent of the resins in the blend being said polypropylene resin, said backsheet being characterized by having a transverse direction tensile strength value at 10 percent elongation of at least 515 grams and a 120° tape adhesion value of at least 380 grams whereby an adhesive tab fastener is attachable and non-destructably detachable from said backsheet.

13. The backsheet of claim 12 wherein said polyethylene comprises more than one-half of the blend.

14. The backsheet of claim 12 wherein the polypropylene comprises about 5 to 25 weight percent of the blend.

15. The backsheet of claim 12 wherein the polypropylene comprises about 10 to 20 weight percent of the blend.

16. The backsheet of claim 12 wherein the backsheet has a gauge of about 1.0 to about 1.5 mils.

17. The backsheet of claim 12 wherein said backsheet has a 120° tape adhesion value of at least about one pound (about 454 grams).

18. The backsheet of claim 12 wherein the backsheet is an embossed monolayer blown film having a nominal thickness of about 1.0 to 1.5 mils made from a resin blend of LDPE and polypropylene, the polypropylene constituting about 5 to about 25 weight percent of the blend.

19. The backsheet of claim 12 wherein the backsheet is a multilayer film having a core of at least 50 weight percent polypropylene and having an outer coating of said blend and a color pigment.

20. A moisture-impervious backsheet for refastenable disposable diapers consisting of a sheet of thermoplastic film consisting essentially of about 3 to about 30 percent polypropylene resin, a color pigment in an amount sufficient to obtain a desired color of the backsheet, and the balance being a polyethylene resin selected from the group consisting of LDPE, LLDPE, LMDPE or a mixture of any two of the foregoing, and a slip additive, said backsheet having a gauge of about 1.0 to 1.5 mils and having a transverse tensile strength value at low elongations of at least about one pound (about 454 grams) and a tab peel force value of at least one pound (about 454 grams), whereby an adhesive tab fastener is attachable and non-destructably detachable from said backsheet.

* * * * *